(12) United States Patent
Krueger et al.

(10) Patent No.: US 9,717,551 B2
(45) Date of Patent: Aug. 1, 2017

(54) INTRAVERTEBRAL TISSUE ABLATION DEVICE AND METHOD

(71) Applicant: CareFusion 2200, Inc., San Diego, CA (US)

(72) Inventors: John A. Krueger, Indian Creek, IL (US); Evan D. Linderman, Deerfield, IL (US); David A. Schechter, Boulder, CO (US); Michael P. Hogan, Grand Junction, CO (US); Michael C. Moses, Denver, CO (US); Joshua K. Goetz, Boulder, CO (US); Nathan H. White, Longmont, CO (US)

(73) Assignee: CareFusion 2200, Inc., San Diego, CA (US)

( * ) Notice: Subject to any disclaimer, the term of this patent is extended or adjusted under 35 U.S.C. 154(b) by 332 days.

(21) Appl. No.: 13/773,114

(22) Filed: Feb. 21, 2013

(65) Prior Publication Data
US 2014/0236144 A1   Aug. 21, 2014

(51) Int. Cl.
*A61B 18/00* (2006.01)
*A61B 18/14* (2006.01)
(Continued)

(52) U.S. Cl.
CPC ........ *A61B 18/148* (2013.01); *A61B 18/1477* (2013.01); *A61B 2017/00455* (2013.01);
(Continued)

(58) Field of Classification Search
CPC ............ A61B 17/8819; A61B 17/1671; A61B 18/148; A61B 2018/00339;
(Continued)

(56) References Cited

U.S. PATENT DOCUMENTS

| 5,334,193 A | 8/1994 | Nardella |
| 5,342,357 A | 8/1994 | Nardella |

(Continued)

FOREIGN PATENT DOCUMENTS

| GB | 2488603 | 9/2012 |
| WO | WO 01/70114 A1 | 9/2001 |
| WO | WO 2011/137377 A1 | 11/2011 |

OTHER PUBLICATIONS

Belifore, G. et al., "Radiofrequency ablation of bone metastases induces long-lasting palliation in patients with untreatable cancer," Singapore Med. J., vol. 49(7), 2008, pp. 565-570.

(Continued)

*Primary Examiner* — Christopher D Koharski
*Assistant Examiner* — Pamela M Bays
(74) *Attorney, Agent, or Firm* — Brinks Gilson & Lione

(57) ABSTRACT

A tissue ablation device is provided for use in soft tissue and/or in bone. It is configured to include an inner probe with a first electrode and a second electrode and an outer needle through which the inner probe extends. After the inner probe is directed therewithin to a target, the outer needle can be withdrawn to expose space between the first and second electrodes to form an RF or other energy field for tissue ablation therebetween upon actuation of an energy source. Such embodiments may include methods for tissue ablation and placement of stabilizing materials.

17 Claims, 9 Drawing Sheets

(51) Int. Cl.
*A61B 17/00* (2006.01)
*A61B 90/00* (2016.01)

(52) U.S. Cl.
CPC .............. *A61B 2017/00867* (2013.01); *A61B 2018/00196* (2013.01); *A61B 2018/00339* (2013.01); *A61B 2018/00577* (2013.01); *A61B 2018/1475* (2013.01); *A61B 2018/1497* (2013.01); *A61B 2090/0811* (2016.02)

(58) Field of Classification Search
CPC ........... A61B 2018/00565; A61B 2018/00577; A61B 2018/00791; A61B 18/1477
USPC ........................................................ 606/41
See application file for complete search history.

(56) References Cited

U.S. PATENT DOCUMENTS

| | | | |
|---|---|---|---|
| 5,348,554 | A | 9/1994 | Imran et al. |
| 5,431,649 | A | 7/1995 | Mulier et al. |
| 5,545,161 | A | 8/1996 | Imran |
| 5,620,447 | A | 4/1997 | Smith et al. |
| 5,672,173 | A * | 9/1997 | Gough ............... A61B 18/1477 606/41 |
| 5,697,927 | A | 12/1997 | Imran et al. |
| 5,833,632 | A | 11/1998 | Jacobsen et al. |
| 6,106,524 | A | 8/2000 | Eggers et al. |
| 6,425,887 | B1 * | 7/2002 | McGuckin ......... A61B 17/3417 604/272 |
| 6,464,683 | B1 | 10/2002 | Samuelson et al. |
| 6,506,189 | B1 | 1/2003 | Rittman, III et al. |
| 7,022,133 | B2 | 4/2006 | Yee et al. |
| 7,713,273 | B2 | 5/2010 | Krueger et al. |
| 7,799,035 | B2 | 9/2010 | Krueger et al. |
| 7,922,690 | B2 | 4/2011 | Plishka et al. |
| 8,021,037 | B2 | 9/2011 | Krueger et al. |
| 8,128,633 | B2 | 3/2012 | Linderman et al. |
| 8,226,657 | B2 | 7/2012 | Linderman et al. |
| 8,277,506 | B2 | 10/2012 | Krueger et al. |
| 2003/0208220 | A1 * | 11/2003 | Worley et al. ................. 606/190 |
| 2006/0189979 | A1 * | 8/2006 | Esch et al. ...................... 606/49 |
| 2007/0118142 | A1 * | 5/2007 | Krueger et al. ................. 606/92 |
| 2008/0140169 | A1 * | 6/2008 | Imran ................... A61N 1/0551 607/117 |
| 2008/0188849 | A1 | 8/2008 | Goldberg et al. |
| 2008/0228192 | A1 | 9/2008 | Beyar et al. |
| 2009/0198232 | A1 * | 8/2009 | Young et al. ................... 606/41 |
| 2010/0204690 | A1 * | 8/2010 | Bigley et al. ................... 606/41 |
| 2010/0211076 | A1 | 8/2010 | Germain et al. |
| 2010/0324506 | A1 * | 12/2010 | Pellegrino et al. ............ 604/272 |
| 2011/0004220 | A1 | 1/2011 | Krueger et al. |
| 2011/0295261 | A1 | 12/2011 | Germain |
| 2011/0295262 | A1 | 12/2011 | Germain et al. |
| 2012/0239047 | A1 | 9/2012 | Linderman et al. |
| 2012/0277753 | A1 | 11/2012 | Linderman et al. |
| 2013/0006232 | A1 | 1/2013 | Pellegrino et al. |

OTHER PUBLICATIONS

Buy, Xavier et al., "Saline-Infused Bipolar Radiofrequency Ablation of High-Risk Spinal and Paraspinal Problems," AJR, vol. 186, May 2006, pp. S322-S326.

Gangi, A. et al., "Quality Improvement Guidelines for Bone Tumour Management," Cardiovasc. Intervent. Radiol., vol. 33, 2010, pp. 706-713.

Gangi, Afshin et al., "Percutaneous Bone Tumor Management," Semin. Intervent. Radiol., vol. 27, 2010, pp. 124-136.

Georgy, B.A. et al., "Plasma-Mediated Radiofrequency Ablation Assited Percutaneous Cement Injection for Treating Advanced Malignant Vertebral Compression Fractures," AJNR, vol. 28, Apr. 2007, pp. 700-705.

Halpin, Ryan J. et al., "Minimally Invasive Treatments for Spinal Metastases: Vertebroplasty, Kyphoplasty, and Radiofrequency Ablation," J. Support. Oncol., vol. 2, No. 4, Jul./Aug. 2004, pp. 339-355.

Jones, Jonathan O. et al., "Management of Painful Vertebral Hamangiomas with Kyphoplasty: A Report of Two Cases and a Literature Review," Pain Physician J., vol. 12, 2009, pp. E297-E303.

Katonis, Pavlos et al., "Treatment of pathologic spinal fractures with combined radiofrequency ablation and balloon kyphoplasty," World Journal of Surgical Oncology, vol. 7:90, 2009, pp. 1-8.

Lane, Michael David et al., "Combination radiofrequency ablation and cementoplasty for palliative treatment of painful neoplastic bone metastasis: experience with 53 treated lesions in 36 patients," Skeletal Radiol., vol. 40, 2011, pp. 25-32.

Masala, S. et al., "Percutaneous ablative treatment of metastatic bone tumours: visual analogue scale scores in a short-term series," Singapore Med. J., vol. 52(3), 2011, pp. 182-189.

Schaefer, Oliver et al., "Combined Treatment of a Spinal Metastasis with Radiofrequency Heat Ablation and Vertebroplasty," AJR, vol. 180, Apr. 2003, pp. 1075-1077.

Thanos, L. et al., "Radiofrequency ablation of osseous metastases for the palliation of pain," Skeletal Radiol., vol. 37, 2008, pp. 189-194.

Unknown author, "MutliGen™—One machine. Four lesions. Multiple Options.," Stryker Interventional Spine, Product brochure, 2008, 8 pages.

* cited by examiner

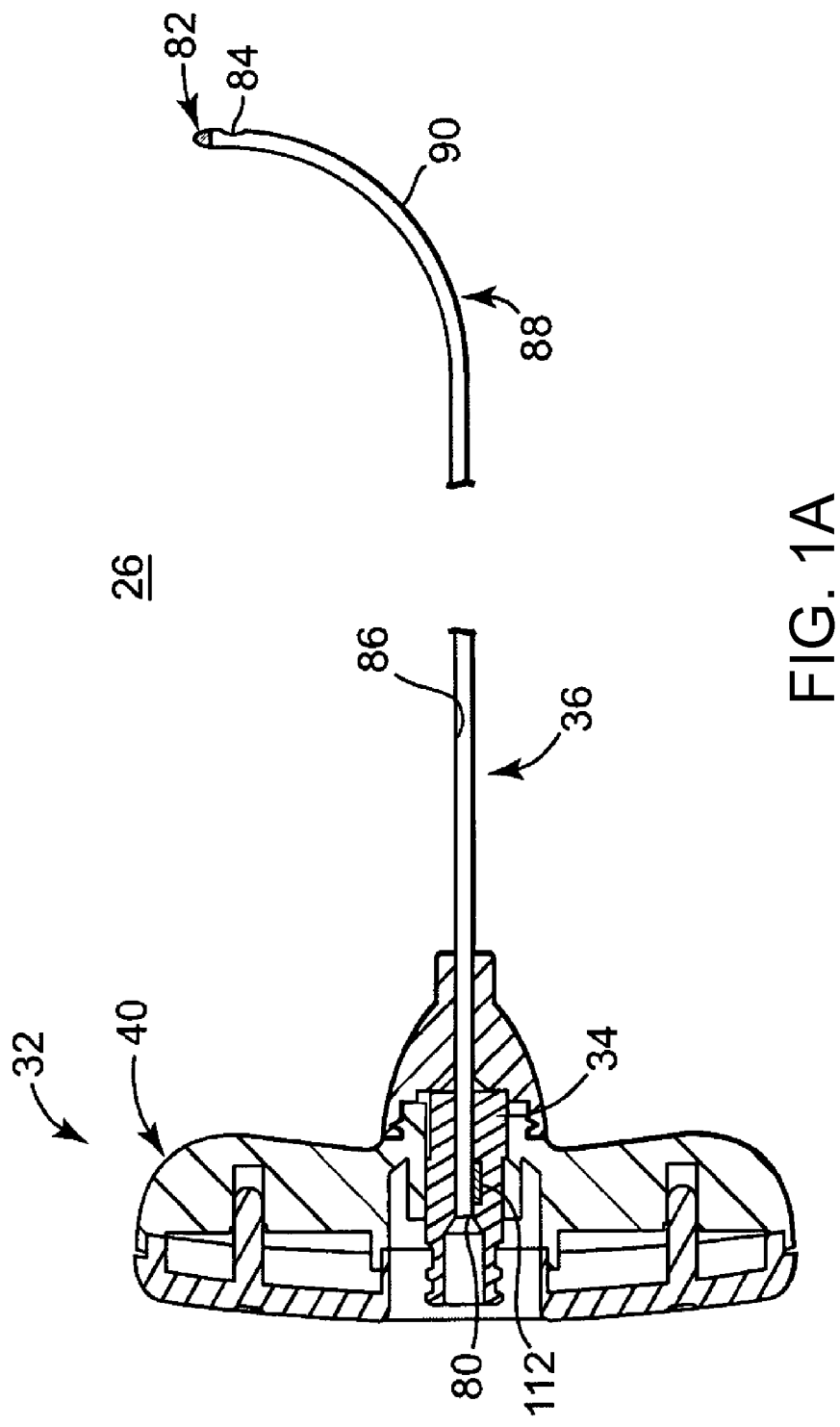

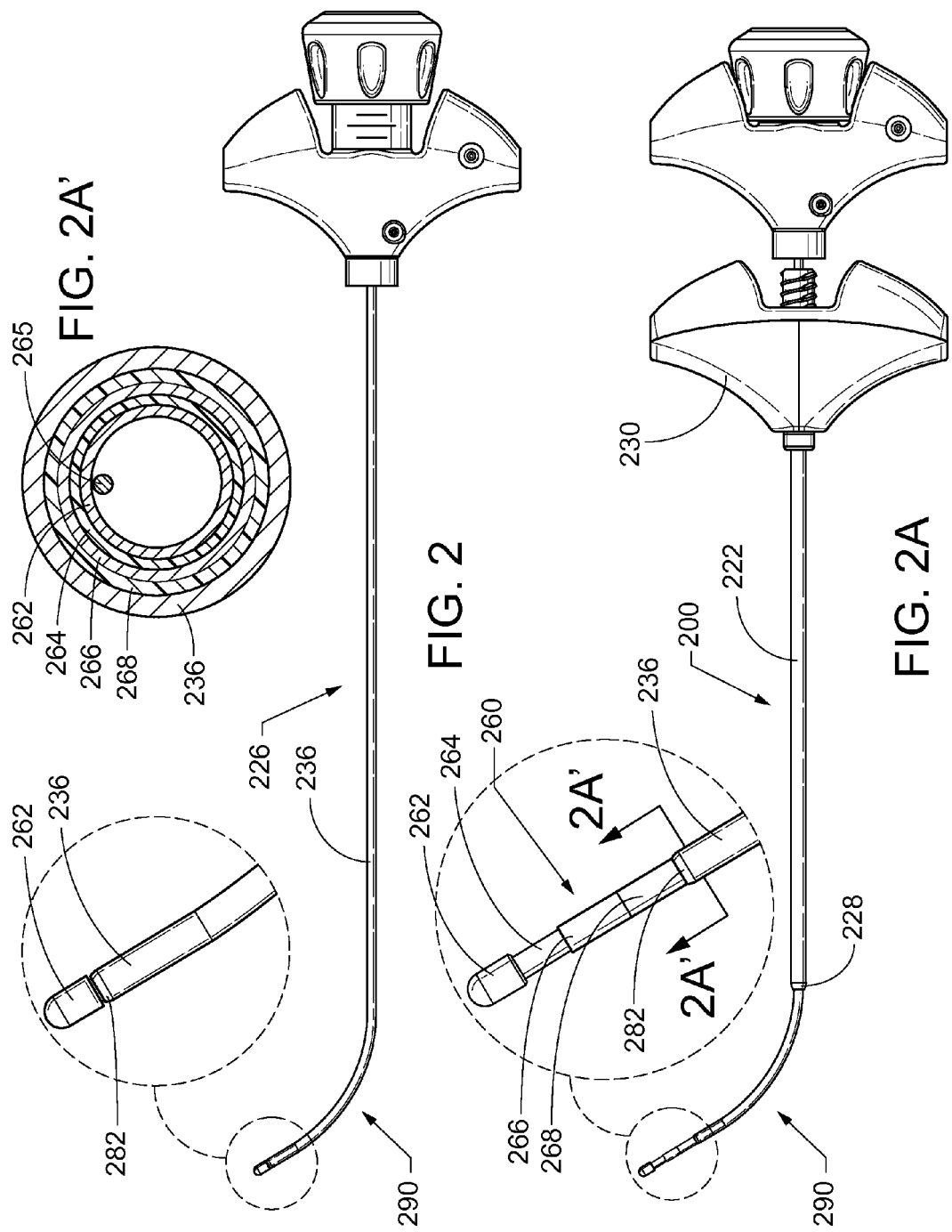

INTRAVERTEBRAL TISSUE ABLATION DEVICE AND METHOD

TECHNICAL FIELD

Embodiments disclosed herein generally relate to devices and methods for stabilizing bone structures. More particularly, the present disclosure relates to devices, systems and methods for delivering a curable, stabilizing material into a bone structure after intravertebral tissue ablation.

BACKGROUND

Surgical intervention at damaged or compromised bone sites has proven highly beneficial for patients, for example patients with back pain associated with vertebral damage. One of the most common types of damage, particularly in patients with osteoporosis, is associated with vertebral compression fractures (VCF).

Bones of the human skeletal system include mineralized tissue that can generally be categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae." Both structures may be weakened by osteoporosis, and compression fractures may occur that distort a vertebra (generally along its vertical axis), which can cause great pain.

During certain bone procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement). In other procedures, percutaneous injection of stabilization material into vertebral compression fractures by, for example, transpedicular or parapedicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible material. Indeed, bone structure may be strengthened and at least partially restored (e.g., restoration of vertebral height/thickness previously lost to VCF) by these procedures. Exemplary devices and methods are summarized herein, and are disclosed in greater detail in U.S. Pat. Nos. 7,713,273; 7,799,035; 7,922,690; 8,021,037; 8,128,633; 8,226,657; and 8,277,506; as well as U.S. Pat. Publ. Nos. 2011/00044220; 2012/0239047; and 2012/0277753, each of which is incorporated herein by reference in its entirety (although, to the extent there is any discrepancy, the present disclosure shall prevail unless there is a clearer alternative).

The conventional technique for delivering the bone stabilizing material entails employment of a straight access device or cannula that bores (or otherwise cuts) through the cortical bone to gain access to the cancellous bone site. Bone stabilization material is then driven through the cannula to fill a portion of the cancellous bone at the bone site. As an intermediate step, a cavity may be created within the bone by inflating a balloon therein and/or by mechanically disrupting the bone by rotating a curved cannula. This may provide for greater penetration and stabilizing effect of the bone stabilization material. To minimize invasiveness of the procedure, the cannula is typically a small diameter needle.

With the above in mind, because the needle cannula interacts with the cancellous bone and other soft tissue structures, an inherent risk exists that following initial insertion, the needle cannula might core or puncture other tissue and/or the bone mass being repaired (at a location apart from the insertion site). Thus, during percutaneous vertebroplasty, great care must be taken to avoid puncturing, coring, or otherwise rupturing the vertebral body. Similar post-insertion coring concerns arise in other interior bone repair procedures. Along these same lines, to minimize trauma and time required to complete the procedure, it is desirable that only a single bone site insertion be performed. Unfortunately, for many procedures, the surgical site in question cannot be fully accessed using a conventional, straight needle cannula. For example, with vertebroplasty, the confined nature of the inner vertebral body oftentimes requires two or more insertions with the straight needle cannula at different vertebral approach locations ("bipedicular" technique). It would be desirable to provide a system for delivering bone stabilizing material that can more readily adopt to the anatomical requirements of a particular delivery site, for example a system capable of promoting unipedicular vertebroplasty.

Certain currently-available instruments utilize a curved needle to deliver bone stabilizing material as part of vertebroplasty or similar procedure. The curved needle purportedly enhances a surgeon's ability to locate and inject the stabilizing material at a desired site. Similar to a conventional straight needle cannula, the curved needle dispenses the curable material through a single, axial opening at the distal-most tip. However, the curved needle is used in combination with an outer cannula that assists in generally establishing access to the bone site as well as facilitating percutaneous delivery of the needle to the delivery site (within bone) in a desired fashion. More particularly, the outer cannula first gains access to the bone site, followed by distal sliding of the needle through the outer cannula.

These existing techniques have proven effective for treatment of certain VCF and other degenerative bone conditions. However, those bone conditions that may benefit from vertebroplasty and/or balloon-vertebroplasty (a/k/a "kyphoplasty") can include other disease conditions. For example metastatic tumors (e.g., those originating from prostate cancer or another primary cancer location), benign tumors, and/or other tissue masses may occur within bone such as a vertebra and cause or co-exist with a fractured condition or other degenerative condition that could be benefited by treatment with bone-stabilization material. In the past, certain techniques would encapsulate such a tumor or tissue mass within the bone-stabilization material. Cryoablation has also been used, as has some application of radiofrequency (RF) ablation. For example, U.S. Pat. Publ. No. 2010/00211076 to Germain et al. discloses an RF ablation device that uses a segmented/linkage-curved needle electrode. However, existing needles may be limited with regard to manipulability and ease of use within intravertebral space.

A need exists for an improved device and system for ablating tissue within bone and/or other tissue sites in a targeted manner, and—if appropriate—thereafter delivering stabilizing material to those sites.

BRIEF SUMMARY

In one aspect, embodiments disclosed herein may include a tissue ablation device for use in soft tissue and/or in bone configured to include an inner probe with a first electrode and a second electrode, an outer needle through which the inner probe extends. After the inner probe is directed therewithin to a target, the outer needle can be withdrawn to expose space between the first and second electrodes to form an RF field for tissue ablation therebetween upon actuation of an RF source. Such embodiments may include methods for tissue ablation and placement of stabilizing materials.

In another aspect, embodiments disclosed herein may include a tissue ablation device for use in soft tissue and/or in bone, with an inner probe with a first electrode and an outer needle with a second electrode through which the inner probe extends and which—after the inner probe is directed therewithin to a target—can be withdrawn to create sufficient space between the first and second electrodes to form an RF or other energy field for tissue ablation therebetween. Such embodiments may include methods for tissue ablation and placement of stabilizing materials. In another aspect, embodiments may include a single inner probe electrode for use in a monopolar configuration with a dispersive return electrode (not presently disclosed, but known in the art).

Certain embodiments, in another aspect, may relate to a kit for intravertebral tissue ablation followed by Kyphoplasty and/or vertebroplasty, where the kit includes one or more of a guide cannula, pre-curved memory metal tissue ablation needle, Kyphoplasty balloon, and vertebroplasty injection needle configured for injecting PMMA or another suitable material (which may be a curable material) for bone stabilization.

BRIEF DESCRIPTION OF THE DRAWINGS

FIG. 1A shows a longitudinal section view to illustrate internal components of one embodiment of the components in FIG. 1;

FIG. 2 shows a tissue ablation needle embodiment, including a detail view of its distal end;

FIG. 2A shows the tissue ablation needle embodiment of FIG. 2, disposed through a guide cannula, including a detail view of its distal end with an inner probe exposed therefrom;

FIG. 2A' shows a transverse section view of FIG. 2A, taken along line 2A'-2A';

DETAILED DESCRIPTION

Figure 1:
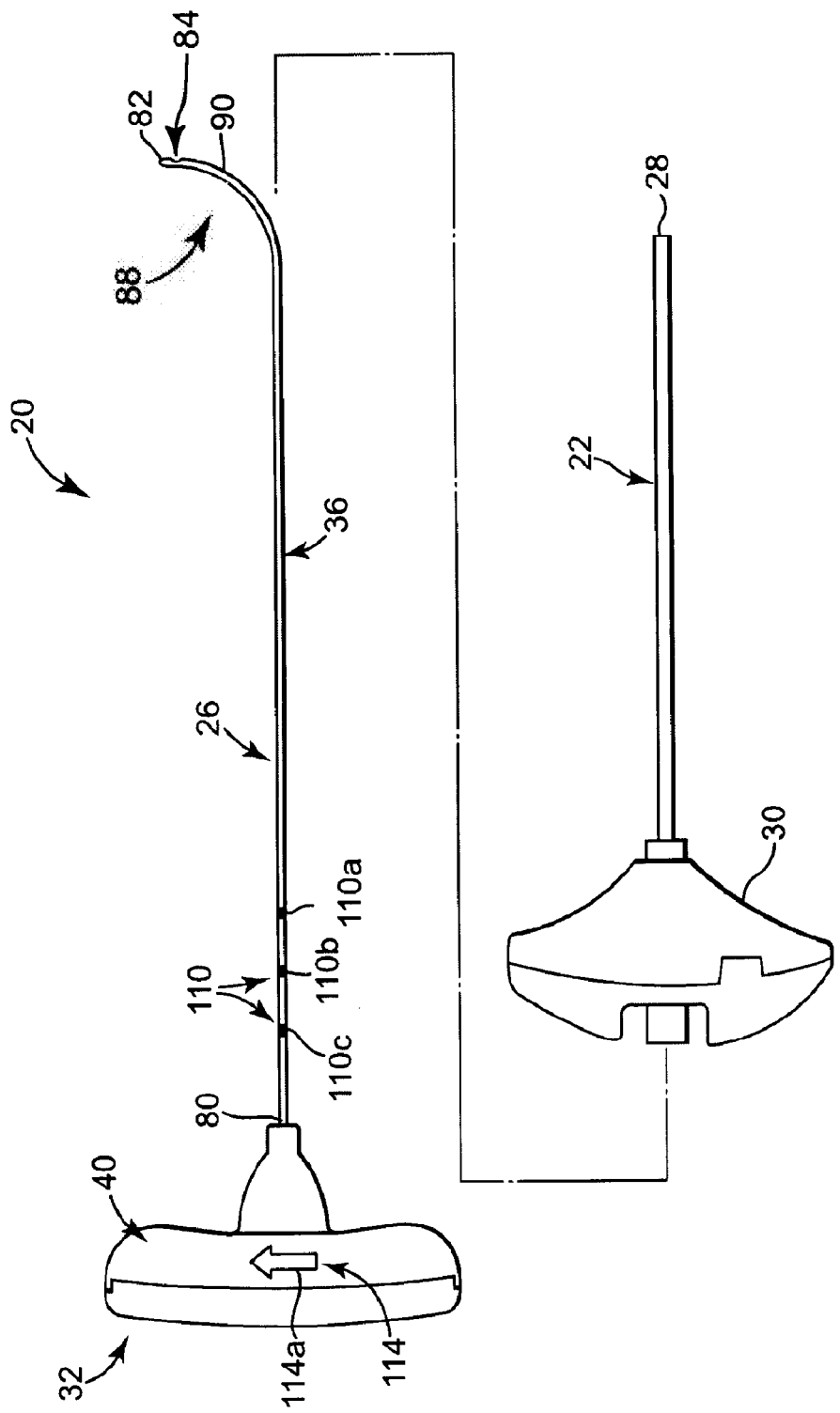
FIG. 1 illustrates components of an intraosseous curable material delivery system.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The terms "proximal" and "distal" are used herein in a common usage sense where they refer respectively to a handle/doctor-end of a device or related object and a tool/patient-end of a device or related object. The terms "degrade" and "denature" are to coagulation necrosis of tissue, resulting in denaturization of collagen or the loss of cellular nuclei. The term "ablate" is used herein in a common medical usage sense to refer to heating and shrinking of tissue by desiccation or by denaturization of collagen, but may be interpreted broadly to include degradation and denaturization.

FIGS. 1-1A illustrate components of one embodiment of an intraosseous, curable material delivery system 20. The system 20 includes an outer guide cannula 22 and a delivery cannula device 26 (referenced generally). The outer guide cannula 22 will be discussed below for use as an access cannula with reference to a tissue ablation system. Details on the various components are provided below. In general terms, however, a portion of the delivery cannula device 26 is sized to be slidably disposed within the guide cannula 22 that otherwise serves to form and/or locate a desired delivery site within bone. Once positioned, the delivery cannula device 26 is employed to inject a curable, bone stabilizing material into the delivery site. The system 20 can be used for a number of different procedures, including, for example, vertebroplasty and other bone augmentation procedures in which curable material is delivered to a site within bone, as well as to remove or aspirate material from a site within bone.

The system 20, and in particular the delivery cannula device 26, is highly useful for delivering a curable material in the form of a bone cement material or other bone stabilization material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable polymethylmethacrylate (PMMA) bone cement, which has a flowable state wherein it can be delivered (e.g., injected) by a cannula to a site and subsequently cures into hardened cement. Other materials, such as calcium phosphates, bone in-growth material, antibiotics, proteins, etc., could be used in place of or to augment, PMMA (but do not affect an overriding characteristic of the resultant formulation having a flowable state and a hardened, solid or cured state). This would allow the body to reabsorb the cement or improve the clinical outcome based on the type of filler implant material. With this in mind, and in one embodiment, the system 20 further includes a source (not shown) of curable material fluidly coupled to the delivery cannula device 26.

Given the above, the outer guide cannula 22 generally enables access of the delivery cannula device 26 to a bone site of interest, and thus can assume a wide variety of forms. In general terms, however, the lumen of the guide cannula 22 is sized to slidably receive a portion of the delivery cannula device 26, terminating in an open, distal tip 28. The distal tip 28 can further be adapted to facilitate coring of bone tissue, such as when using the guide cannula 22 to form a delivery site within bone. A solid-tipped trocar or stylet (not shown) with a penetrating (e.g., beveled, drill-threaded, or otherwise pointed) tip may be extended through the cannula distal tip 28 to facilitate penetrating bone and/or other tissue without significant coring.

To promote a desired interface between the guide cannula 22 and a portion of the delivery cannula device 26 otherwise slidably inserted within the guide cannula 22 during use (described below), in one embodiment, an inner diameter surface of the guide cannula 22 is highly smoothed to a matte or mirror finish (i.e., RMS range of about 0-16). In another preferred embodiment, the inner diameter surface of the guide cannula 22 or the outer diameter surface of the delivery cannula 36 can be coated with Teflon to promote a smooth desired interface between the guide cannula 22 and a portion of the delivery cannula device 26 otherwise slidably inserted within the guide cannula 22 during use. A Teflon sleeve between the guide cannula 22 and a portion of the delivery cannula device 26 may also be used. Further, the outer diameter surface of the delivery cannula 36 can be polished to a highly smoothed to a matte or mirror finish (i.e., RMS range of about 0-16). Regardless, and in some embodiments, the guide cannula 22 can further be attached, at a proximal end thereof, to a handle 30 for enhancing a surgeon's ability to manipulate the system 20. Alternatively, the handle 30 may be eliminated.

Certain details of the delivery cannula device 26 are shown in greater detail in FIG. 1A, and generally includes a handle assembly 32 (referenced generally), a hub 34, and a delivery cannula 36. The hub port 34 forms a fluid port and is fluidly connected to the delivery cannula 36, with the handle assembly 32 retaining the combination hub 34/delivery cannula 36. As described in greater detail below, the delivery cannula 36 is sized to be coaxially, slidably received within the guide cannula 22, and is configured to deliver a curable material injected therein via the hub 34.

The handle assembly 32 includes, in some embodiments, a handle 40, which incorporates the hub 34 and secures the delivery cannula 36 to the handle 40. To provide enhanced stability at the hub 34/delivery cannula 36 interface, a support body 112 may be secured to the delivery cannula 36 adjacent the proximal delivery cannula end 80 (referenced generally in FIG. 1 and more particularly in FIG. 1A). If used, the support body 112 preferably is a rigid material amenable to secure attachment to the delivery cannula 36 material (e.g., where the delivery cannula 36 is formed of nitinol, the support body 112 can also be formed of nitinol and thus easily welded to the delivery cannula 36). The support body 112 embodiment is rectangular (a thickness on the order of 0.035 inch, width on the order of 0.05 inch, and a length on the order of 0.2 inch, although other dimensions are acceptable) so that when applied to the otherwise circular (in transverse cross-section) delivery cannula 36, the support body 112 provides flat surfaces onto which the hub 34 may be overmolded. This flat surface area interface, in turn, overtly resists "slipping" of the hub 34 relative to the delivery cannula 36 and vice-versa in response to a tensile, compressive, and/or torsional force(s) placed on either component.

The hub 34 is mounted within the handle assembly 32 as shown. This configuration of the handle assembly 32 dictates that the delivery cannula bend 90 will also extend in a known spatial direction relative to the handle 40. Regardless, in some embodiments (e.g., as shown in FIG. 1), the handle assembly 32 further includes directional indicia 114 (referenced generally) along an exterior of the handle 40 that provides a user with an indication of the bend 90 direction relative to the handle 40. For example, in one embodiment, the directional indicia 114 includes an arrow 114a pointing at the direction of distal tip delivery cannula tip 82 as oriented by the bend 90. With this configuration, a user can readily ascertain a spatial positioning of the bend 90 relative to the handle 40 when the bend 90 is inserted within the confines of a surgical site (and thus not otherwise visible to the user). The directional indicia 114 can be applied at various locations along the handle 40 such as on both major faces (one of which is visible in FIG. 1) as well as a proximal end thereof, and can assume a variety of forms.

The delivery/injection cannula 36 defines a proximal end 80 and a distal end 82, and forms one or more side orifices 84 adjacent the distal end 82 and in fluid communication with a delivery cannula lumen 86. In the illustrated embodiment, a single orifice 84 is provided, and is opposite (that is, along an outside-facing surface relative to a direction of the bend 90). the delivery cannula 36 includes a deflectable segment 88 (referenced generally) defining a pre-set curve or bend 90. As described below, the deflectable segment 88, and in particular the bend 90, includes or extends from the distal end 82, and has a shape memory attribute whereby the deflectable segment 88 can be forced from the curved shape to a substantially straightened shape such as when being constrained within the confines of a guide cannula, and will naturally revert back to the curved shape upon removal of the force/constraint.

In the illustrated embodiment, the delivery cannula 36 defines a continuous length between the proximal end 80 and the distal end 82, with the memory metal pre-set curved, deflectable segment 88, and in particular the bend 90, extending along approximately 25% of the length from the distal end 82. In other embodiments suited for other surgical procedures, the deflectable segment 88, and in particular the bend 90 may extends along between about 10% to about 50% of the length of the delivery cannula 36 as measured from the distal end 82, which (as with the other aspects of the delivery cannula described here) is true also for the outer needle of the tissue ablation system described below.

To facilitate delivery of a curable material (e.g., bone cement) into a confined site within bone (such as with a vertebroplasty procedure), the deflectable segment 88 can be formed to define the bend 90 at a pre-determined radius of curvature appropriate for the procedure in question. Further, to facilitate ready deflection of the deflectable segment 88 from the curved shape to a substantially straightened state (such as when the delivery cannula 36 is inserted within the outer guide cannula 22) and reversion back to the curved shape, the delivery cannula 36, or at least the deflectable segment 88, is formed of a shape memory metal. In one embodiment, the delivery cannula 36 may include Nitinol™, a known shape memory alloy including nickel (Ni) and titanium (Ti). In some embodiments, the bend 90 may be formed in the delivery cannula 36 by deforming a straight fluid delivery cannula under extreme heat for a prescribed period of time, which pre-sets a curved shape in the delivery cannula 36. In other embodiments, the pre-set curve or bend 90 may be formed in an initially straight cannula by cold working the straight cannula and applying a mechanical stress. Cold working of suitable memory metal materials may permanently lock a crystalline structure (for example, a partial martensitic crystalline structure) in a portion (i.e., the deflectable segment 88) of the cannula, while an unstressed portion remains in, for example, an austenitic structure. In addition to Nitinol, other materials exhibiting this shape memory behavior can be employed, including superelastic or pseudoelastic copper alloys, such as alloys of copper, aluminum, and nickel, and alloys of copper, aluminum, and zinc, and alloys of copper and zinc. Regardless, the deflectable segment 88 is formed to be resilient and to naturally assume the desired radius of curvature R. In this manner, after the delivery cannula 36, and in particular the deflectable segment 88, is flexed to a substantially straightened shape (not shown), upon a subsequent relaxation, the deflectable segment 88 remembers the pre-set curved shape and reversibly relaxes/returns to the bend 90.

Another feature of the delivery cannula 36 in accordance with certain embodiments is shown in FIG. 1, where the delivery cannula 36 includes indicia 110 (referenced generally) adjacent the proximal delivery cannula end 80. The indicia 110 are indicative of a location of the delivery cannula distal end 82 relative to the distal tip 28 of the guide cannula 22 upon insertion of the delivery cannula 36 within the guide cannula 22. For example, the indicia 110 can include first, second, and third depth markings 110a, 110b, 110c. A longitudinal location of the first depth marking 110a relative to the distal end 82 is commensurate with a length of the guide cannula 22 in combination with the handle 30. That is to say, the first depth marking 110a is located at a linear distance from the distal end 82 such that upon insertion of the delivery cannula 36 within the guide cannula 22 (otherwise forcing the delivery cannula 36 to a substantially straightened state), when the distal end 82 is at or substantially even with the distal tip 28 of the guide cannula 22, the first depth marking 110a will be proximally adjacent or aligned with (and visible relative to) a proximal side of the handle 30. Thus, a user can quickly and easily have visual confirmation that the distal end 82 is within the guide cannula 22. The second and third depth markings 110b, 110c are proximally spaced from the first depth marking 110a at known increments (e.g., 0.5 cm, 1.0 cm, etc.) that represent length of distal extension of the distal end 82 relative to the distal tip 28. For example, where the second depth marking 110b is longitudinally spaced (proximally) a distance of 0.5 cm from the first depth marking 110a and the third depth marking 110c is spaced 0.5 cm from the second depth marking 110b, during use when the delivery cannula 36 is inserted within the guide cannula 22 such that the second depth marking 110b is aligned with the proximal side of the handle 30, a user can visually confirm (from a location away from the surgical site and outside of the patient) that an approximately 0.5 cm length of the delivery cannula 36 is extending distal the distal tip 28 of the guide cannula 22. Similarly, when the third marking 110c is aligned with the proximal side of the handle 30, an approximately 1.0 cm length of the delivery cannula 36 is exposed distal the distal tip 28.

A tissue ablation system is described with reference to FIGS. 1-1A above and FIGS. 2-4B below. FIGS. 2-2A show components of a tissue ablation needle system 200, including a rigid elongate guide cannula 222 with a hub 230, an open proximal end, an open distal guide cannula end 228, and a guide cannula lumen (not shown) extending between its proximal and distal ends. The system 200 also includes a tissue ablation needle 226 that includes an elongate needle cannula 236 defining a needle lumen (not shown) through which an inner probe 260 extends. At least one of the needle cannula 236, the inner probe 260, or both is/are slidable relative to the other. In FIG. 2, the inner probe 260 (shown more clearly in FIG. 2A) is generally fully engaged within the needle cannula 236, and FIG. 2A shows the inner probe 260 extended relative to the distal end 282 of needle cannula 236 (and/or needle cannula 236 retracted relative to the inner probe 260), with the needle cannula 236 engaged through the guide cannula 222. The guide cannula may be a relatively small-diameter construction (e.g., about 11 gauge), which can provide advantages to directing it through tissue.

Figure 2B:
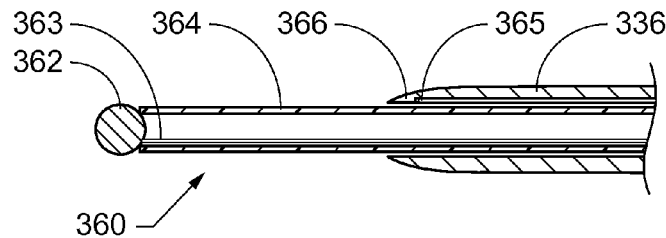
FIGS. 2B-2D show transverse section views of the distal end portion of a tissue ablation needle cannula with different embodiments of an inner probe disposed through the needle cannula lumen.

Like the delivery cannula 26 described above, the needle cannula 236 includes a distal region pre-set, unjointed/continuous memory metal bend or curve 290 that can be substantially straightened to accommodate constrained passage through the guide cannula lumen and that includes a shape memory to assume the pre-set curve when unconstrained. Indicia (not shown, but potentially embodied as in FIG. 1) may be included to show the orientation of the distal region curvature of the needle cannula 236. The inner probe embodiment of FIGS. 2-2A' includes a distal tip/end terminus configured as a first electrode 262. A second electrode 266 is disposed proximal of the first electrode 262, separated therefrom by a first electroinsulative region 264. Preferred insulating materials in this and other embodiments may include, for example, high temperature-resistant (>200° F.) and/or high CTI (comparative tracking index ASTM D3638-12; >300V) materials. A second electroinsulative coating layer 268 separates the second electrode 266 from the needle cannula 236. As shown in FIG. 2A' (which is a transverse section view along line 2A'-2A' of FIG. 2A) and in the longitudinal section views of needle cannula embodiments shown in FIGS. 2B-2D, each of the electrodes 262, 266 and the electroinsulative regions 264, 268 includes an exposed portion (shown in the plan views of FIGS. 2-2A) and a non-exposed portion that extends coaxially within/through proximally-adjacent components. The needle cannula 236 may include one or more temperature sensors (e.g., thermocouple or thermistor) for closed-loop control of energy output to desired setpoint. FIG. 2A' shows a wire 265 in communication with an internal distal temperature sensor (not shown). Such a temperature sensor preferably will be located adjacent the distal electrode 262 to measure temperature at the extents of the E-field. The tissue ablation needle 226 may also include an additional temperature sensor for measuring temperature external to the E-field for the purpose of preventing excess heating to collateral tissue structures. One or more temperature sensor(s) may be incorporated on and/or in needle cannula 236, and/or may be provided as part of an independently/separately placed needle probe (not shown). Energy output to tissue ablation needle 226 may also be controlled base on one or more of the following input parameters: current, impedance, resistance, voltage, phase angle, capacitance or inductance.

The electrodes provide for directing radiofrequency (RF) or Microwave (MW) energy from the first to the second electrode (or vice versa, throughout the present application), creating an E-field that—when the probe is disposed within tissue—will generate sufficient heat to denature/ablate cellular material within the field. The generation of heat in the target tissue zone generally will cause coagulation necrosis so that targeted tissue is irreversibly damaged in a manner desired and controlled to prevent regrowth of targeted tissue. For temperatures between about 40° C. and about 100° C., this is a first order rate limited degradation commonly described by the Arrhenius Equation. Coagulation necrosis occurs by direct resistive heating of the target tissue and by thermal conduction of heat into the zone adjacent the E-field. The target temperature for ablation of tissue is between about 70° C. and about 100° C., preferably about 90° C., and application of energy preferably will be maintained for about (but greater than) 0 to about 300 seconds. A closed-loop controlled modulation of voltage, current or power may be employed. The target control set-point (i.e. temperature) may be maintained by varying duty-cycle of RF output or by macro-pulsing, and it may be monitored by one or more integrated and/or external temperature sensors. Those of skill in the art will recognize the principles of bipolar as well as monopolar and/or microwave ablation applied herein without need for detailed explication. A subset of bipolar RF ablation is plasma-mediated RF ablation. In this process RF energy is applied to sufficiently vaporize a fluid, where an ionized plasma is formed and charged particles are accelerated to cause vaporization and volumetric removal of tissue. A more complete description of this phenomena is described in Eggers et al. U.S. Pat. No. 5,683,366. In the presently described embodiments, electrical conductivity may be improved between the first and second electrode by infusion of an electrically conductive fluid (e.g. isotonic saline) into the target ablation site within the bone. However, based on the spacing of the electrodes and the energy delivery parameters, ionized plasma is not created nor desired.

Figure 2C:
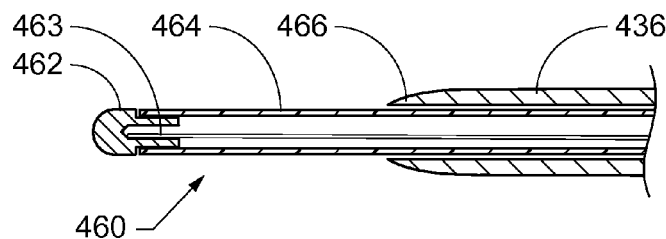
Figure 2D:
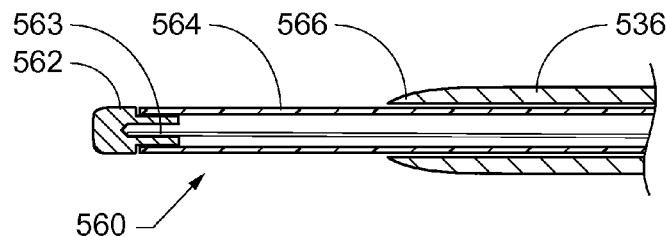

FIGS. 2B-2D show longitudinal section views of the distal end portion of a needle cannula and inner probe disposed through the needle cannula lumen. In each of these embodiments, the second electrode is included in or formed by the distal body of the needle cannula. FIG. 2B shows a needle probe 360 including a distal-end first electrode 362. A first thermocouple 363 may be provided near the first electrode 362 through the probe body. An electroinsulator sleeve 364 forms the proximal length of the probe body to insulate between it and the second electrode 366 formed by or included as part of the distal end of the needle cannula 336 (e.g., as a PEEK extruded body or other polymer construction, preferably with desirable high-temperature tolerance and high CTI, that will serve as electroinsulation). As such, the inner probe may include a metal body coated by an electroinsulative layer, or it may be formed substantially of an electroinsulative material with a separate conductive trace or wire providing a path of communication to the first electrode and, if present as part of the inner probe, other electrodes. A second thermocouple 365 may also be provided. In some embodiments, the first thermocouple may measure temperature at/near the distal end and the second thermocouple may measure temperature at/near the proximal end of and adjacent to the target heating zone around an E-field between electrodes. The second thermocouple may be used for a limit condition to prevent overheating of collateral tissue (e.g., in an intervertebral usage, it may be important not to allow heating beyond a certain point of tissues immediately adjacent to critical neural structures). In this and the following embodiments, it may be desirable to include an electroinsulative cover (not shown) between the needle cannula 336 and an encompassing guide cannula. The distal tip first electrode 362 is constructed in this embodiment as generally spherical (e.g., a machined metal ball, plasma-welded bead).

FIG. 2C shows another embodiment of a needle probe 460 including a distal-end first electrode 462. Electrical current may be transmitted to the distal-end first electrode 462 by the support tube (e.g., in an embodiment constructed including conductive material) or separate conductive trace or wire that may be embedded or otherwise integrated into the sleeve/support tube 464. A first temperature sensor 463 may be provided near the distal terminus or near the first electrode 462 with a communication line (e.g., wire) extending proximally from the sensor. An electroinsulator sleeve 464 forms the proximal length of the probe body to insulate between it and the second electrode 466 formed by the distal end of the needle cannula 436, which functions as a return electrode. In this embodiment, the distal tip first electrode 462 is constructed with a generally hemispherical or parabolic distal exterior. In this and other embodiments where an electrode is included in the needle cannula, it may be desirable to insulate the needle cannula from the guide cannula.

FIG. 2D shows another embodiment of a needle probe 560 including a distal-end first electrode 562. A first thermocouple 563 may be provided. An electroinsulator sleeve 564 may form (or cover) a proximal length of the probe body to insulate between it and the second electrode 566 formed by the distal end of the needle cannula 536, which functions as a return electrode. In this embodiment, the distal tip first electrode 562 is constructed with a blunt-tipped generally cylindrical distal exterior. In this and other embodiments, the second/return electrode may be provided separately (e.g., as a relatively large surface area pad outside a patient body) in the manner well-known in the electrosurgery arts and commonly described as "monopolar."

Figure 2E:
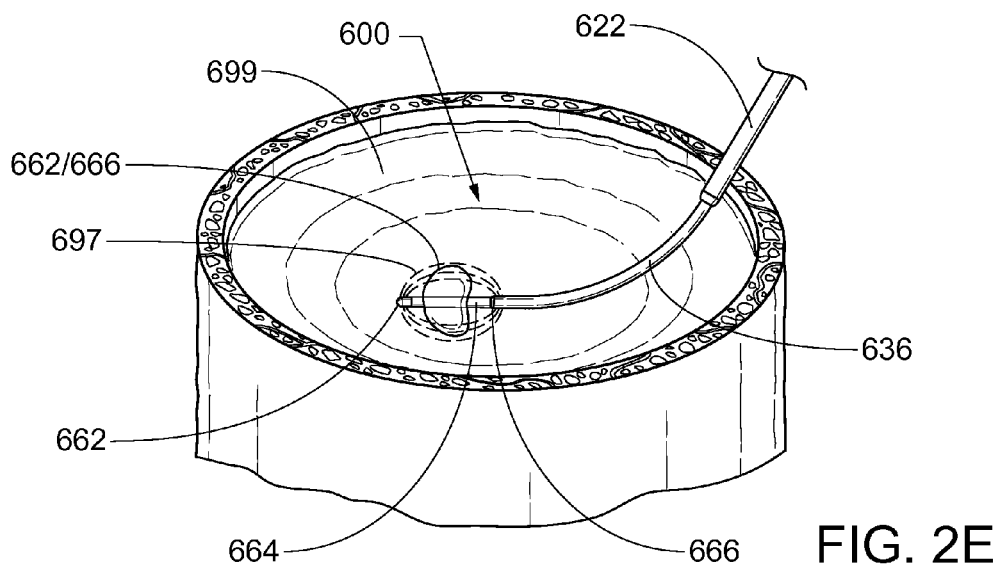
FIG. 2E shows a distal end portion of a tissue ablation needle cannula with an inner probe deployed therefrom within exemplary target tissue.

FIG. 2E shows, in diagrammatic fashion, the deployment of a device tissue ablation needle system 600 embodied like the embodiments of FIGS. 2B-2D. A guide cannula 622 has been used to provide access into a target mass 697 within a tissue region 699. The pre-curved needle cannula 636 has been directed through the access cannula 622 into the tissue mass 699, and then withdrawn from around its inner probe 660 (and/or the inner probe 660 has been extended from the needle cannula 636). The distal terminus of the probe 660 includes a first electrode 662, and the distal terminus of the needle cannula 636 includes a second electrode 666, kept separate from the first electrode 662 by an intervening electroinsulative material 664. Exemplary E-field lines 662/666 are shown between the electrodes, which may be separated by, for example, less than about 0.5 cm to about 2.5 cm. When energized to direct RF or other energy in this manner, the cells of the tissue affected by the energy will degrade or otherwise be disrupted to ablate the target mass 697.

Figure 3A:
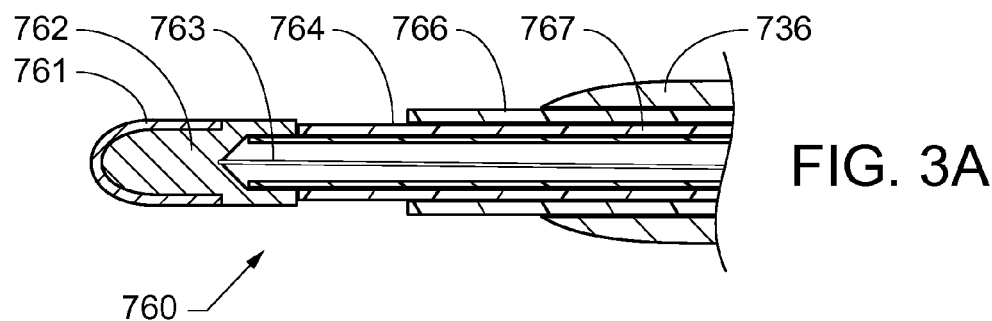
FIGS. 3A-3D show embodiments of a tissue ablation needle assembly with its inner probe including a coated distal tip.

FIG. 3A shows another embodiment, which includes an insulated-tip ablation needle 700. The needle probe 760 including a distal-end first electrode 762, with an insulated/nonconductive coating or construction 761 on the distal tip. An electroinsulator sleeve 764 covers the support tube 767 (e.g., stainless steel hypotube or nitinol tubing) to insulate between first electrode 762 and the second electrode 766 which is formed in this embodiment by hypotube around the electroinsulator sleeve 764 (which hypotube 766 may further include an insulation layer—not shown—between itself and the needle cannula 736). The second electrode 766 may also be a separate band electrode with a secondary conductive trace or wire (not shown) that extends to and provides a communication path for energy from a proximal source (not shown) in the same or similar manner as other electrodes disclosed herein. All of these components are shown extending from the lumen of the needle cannula 736. In FIG. 3A, the distal tip 761 is shown with an outer diameter that may allow it to be withdrawn into the needle lumen, but it should be appreciated that the outer diameter could be constructed to be about the same as or larger than that of the needle cannula 736. A distally-attached thermocouple 763 is also provided and may be present in other embodiments, which may further include one or more other internal and/or external temperature sensors.

Figure 3B:
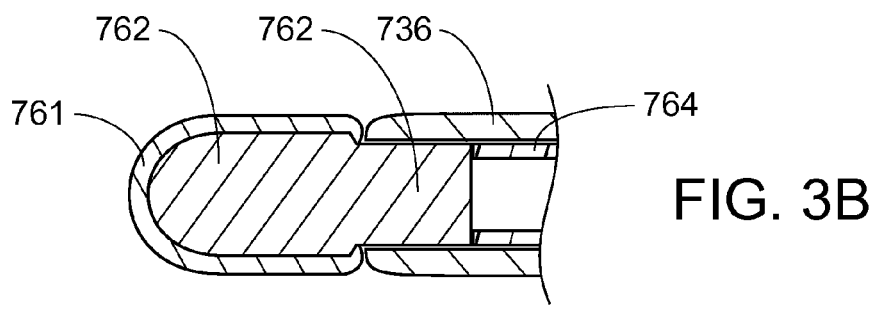
Figure 3C:
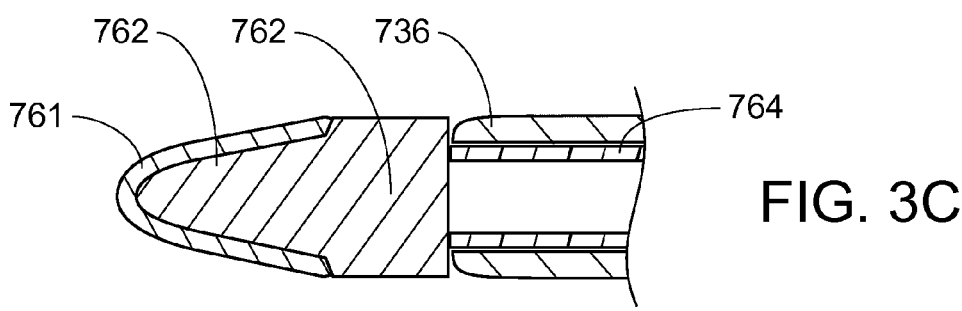
Figure 3D:
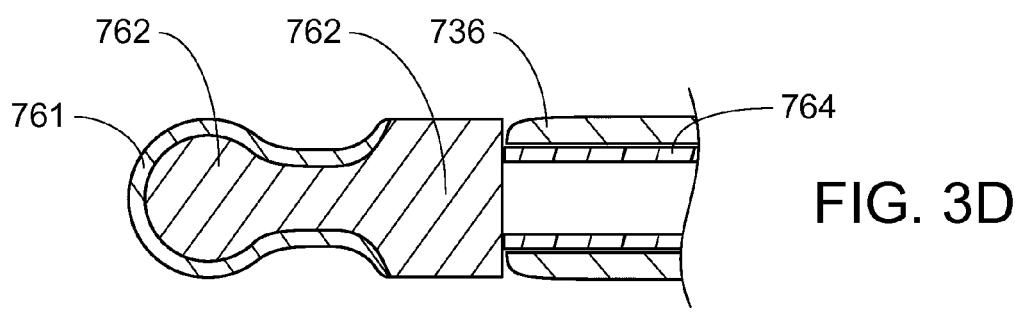

FIGS. 3B-3D show different insulated tip configurations, similar in construction to (and numbered the same as, but different in geometry than) the embodiment of FIG. 3A. In each of these embodiments, the distal tip insulation may be provided by, for example, plasma spray-deposited ceramic (e.g. Alumina Oxide—$Al_2O_3$, Alumina Titania—$Al_2O_3$ $3TiO_2$), a high-temperature thermoset polymer (e.g., polyamide imide), and/or a high-temperature thermoplastic (e.g., PTFE, Kynar™). These and other embodiments herein may further include a support tube 767 and may also include a hypotube second electrode 766 as in FIG. 3A, a second electrode that is incorporated in the probe body like FIG. 2A, or a second electrode included in the needle cannula as illustrated elsewhere in the present disclosure, as well as (like the other embodiments, a third and/or further plurality of electrodes).

In the embodiment of FIG. 3B, the coated distal tip 761 has a larger outer diameter than the first electrode tip portion 762 such that outer diameter of the coated tip is about the same as the needle cannula 736. As shown, the distal tip 761 of the inner probe can form a nearly continuous outer surface with the needle cannula 736. The probe body 764 may have about the same outer diameter as the first electrode portion 762. This and other embodiments preferably will include at least one thermocouple or other temperature sensor.

In the embodiment of FIG. 3C, the coated distal tip 761 is generally conical and has about the same outer diameter (at its base/largest-OD portion) as the first electrode tip portion 762. This generally common outer diameter of the coated tip and electrode is about the same as that of the needle cannula 736. Thus, as shown, the first electrode tip portion 762 of the inner probe can form a nearly continuous outer surface with the needle cannula 736, which may improve tissue penetration, tissue contact during actuation, and may enhance initial impedance of the distal first electrode 762. The probe body 764 may have a smaller outer diameter than the first electrode portion 762, where the probe body's outer diameter is about the same as or only slightly less than the inner diameter of the needle cannula 736.

In the embodiment of FIG. 3D, the coated distal tip 761 is generally bulb-shaped with a smaller-OD portion providing relief and has about the same outer diameter (at its largest-OD portion) as the first electrode tip portion 762 and as the needle cannula 736. Thus, as shown, the first electrode tip portion 762 of the inner probe can form a nearly continuous outer surface with the needle cannula 736. The probe body 763 may have a smaller outer diameter than the first electrode portion 762, where the probe body's outer diameter is about the same as or only slightly less than the inner diameter of the needle cannula 736.

Figure 3E:
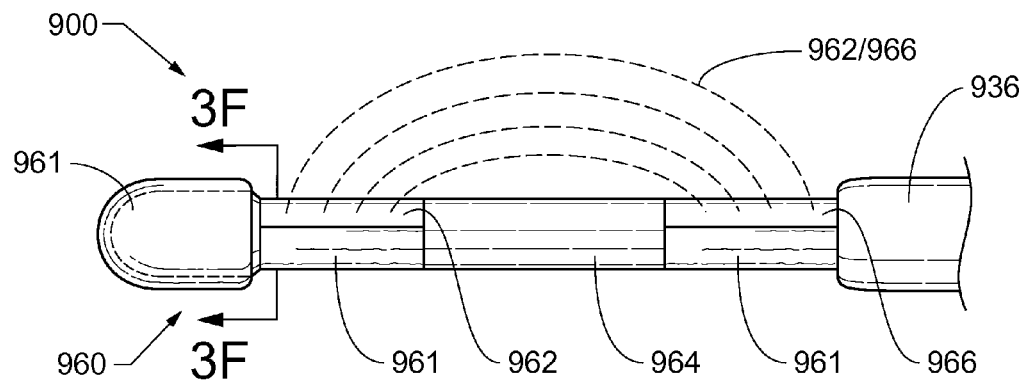
FIGS. 3E-3F show, respectively, plan and transverse section views of a tissue ablation needle assembly with its inner probe that is laterally partially insulated to provide a radially-directional ablation energy field.
Figure 3F:
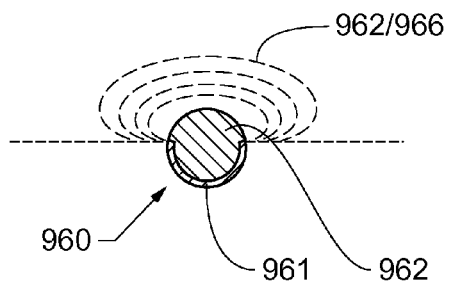

FIGS. 3E-3F depict a "radially-limited field" embodiment of a tissue ablation needle device 900 including an inner probe 960 extending out from a distal end of a needle cannula 936. Similar to the embodiments of FIGS. 3A-3D, and as shown in the plan view of FIG. 3E the inner probe distal tip 961 is coated, but the coating extends proximally longitudinally along a portion of the outer circumference of the probe 960. A first electrode 962 is immediately proximal of the coated distal tip 961. As illustrated (including with reference to FIG. 3F, which is a transverse section view of FIG. 3E along line 3F-3F), the nonconductive tip coating extends along about the lower radial half of the probe body both proximal and distal of a band of electroinsulative material 964 that separates the first electrode 962 from the second electrode 966. This would provide an asymmetrical ablation zone lateral to the active exposed side of the probe. A second electroinsulative region 968 may be provided between the exterior of the probe and the needle cannula 936 (as a lining of the needle cannula lumen and/or an outer coating along the probe body). FIGS. 3E-3F show exemplary field lines 962/966 for general purposes of illustration as to how this embodiment may be used to target and ablate tissue along one side of the inner probe 960. A proximal-end handle of the inner probe (not shown) may be provided to allow rotation about its longitudinal axis and may include indicia of the non-insulated side so that a user can more readily direct the pre-curved needle cannula 936 and the inner probe 960 to a desired location and orientation.

Figure 3G:
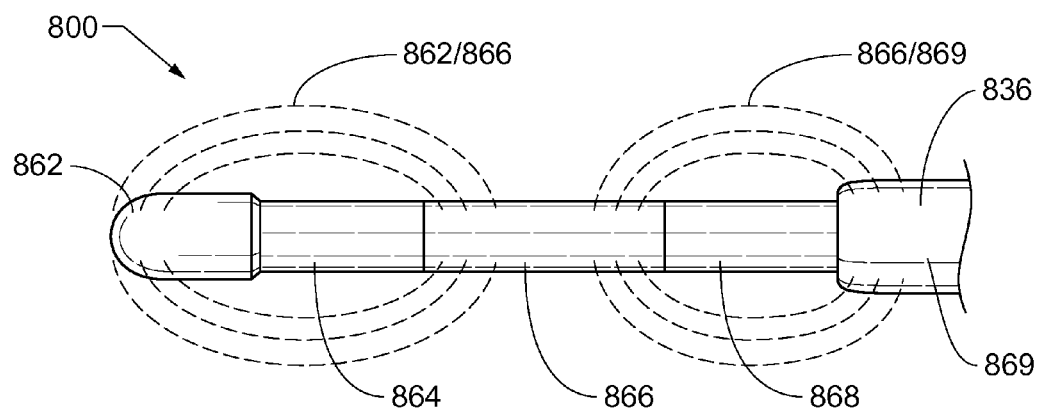
FIG. 3G shows an embodiment of a tissue ablation needle assembly with its inner probe that includes a dual-ablation-field configuration, as one example of a multi-electrode embodiment.

FIG. 3G shows another embodiment, which may provide a multi-electrode dual-field ablation needle 800. The inner probe embodiment of FIG. 3G includes a distal tip/end terminus configured as a first electrode 862. A second electrode 866 is disposed proximal of the first electrode 862, separated therefrom by a first electroinsulative region 864, and a third electrode 869 is disposed proximal of the second electrode 866, separated therefrom by a second electroinsulative region 868. The third electrode 869 is shown as included in the needle cannula 836, but may (as illustrated elsewhere herein) be included as part of the inner probe structure. The electrodes provide for directing radiofrequency (RF) energy from the second to the first and/or third electrode(s), creating a dual RF field that—when the probe is disposed within tissue—will generate sufficient heat to disrupt/ablate cellular material within the field, and potentially between the fields (providing for a longer ablation region without significant increase of ablation diameter). FIG. 3G also shows exemplary field lines 862/866 and 866/869 for general purposes of illustration.

Figure 4:
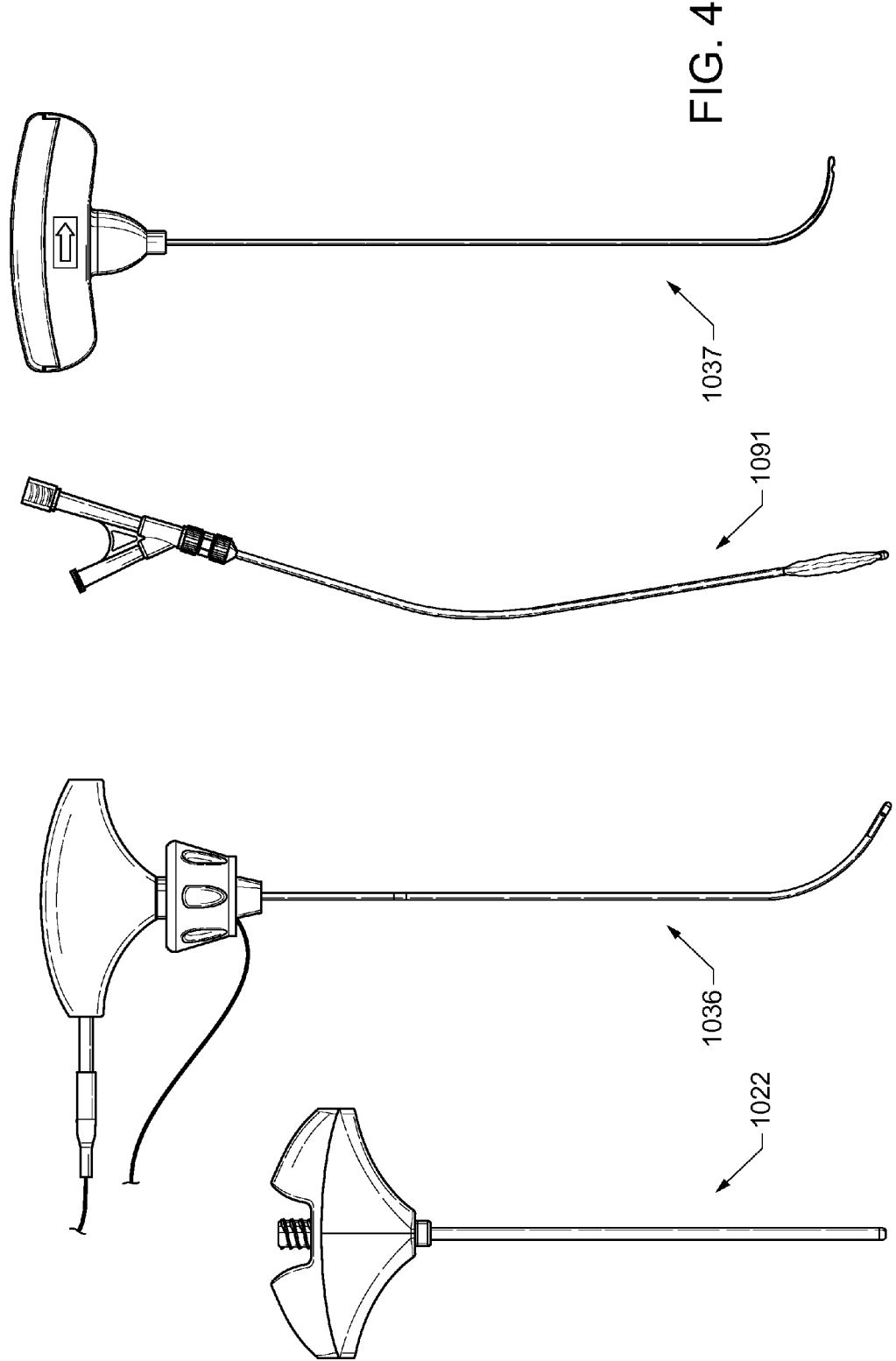
FIG. 4 shows elements of a kit for intravertebral tissue ablation followed by Kyphoplasty and/or vertebroplasty, including a guide cannula, a pre-curved memory metal tissue ablation needle device, a Kyphoplasty balloon assembly, and a curable material delivery device embodied as a vertebroplasty injection needle.

FIG. 4 shows elements of one embodiment a kit for conducting an intervertebral tissue ablation and balloon-assisted vertebroplasty, where a kit may include more or fewer components, but—in keeping with the present disclosure—will generally include at least a pre-curved memory metal tissue ablation needle. A guide cannula 1022 is shown at the left, and may be used with one or more trocar, stylet, drill, and/or other guide cannula accessory elements known and used in the art with such a cannula for penetrating tissue such as accessing intravertebral space (e.g., bone-penetrating guide cannula accessory, available as AVAmax® needles from C are Fusion, Inc. (San Diego, Calif.). A pre-curved memory metal tissue ablation needle 1036 is shown, second from the left. A Kyphoplasty balloon unit 1091 (which may be embodied as AVAmax® Vertebral Augmentation Balloon from C are Fusion, Inc. (San Diego, Calif.) is shown adjacent-right the needle assembly 1036, and a pre-curved memory metal injection needle 1037 (which may be embodied in the manner of FIGS. 1-1A, and/or which may be embodied as an AVAflex® needle from C are Fusion, Inc. (San Diego, Calif.)) is shown on the right.

Figure 4A:
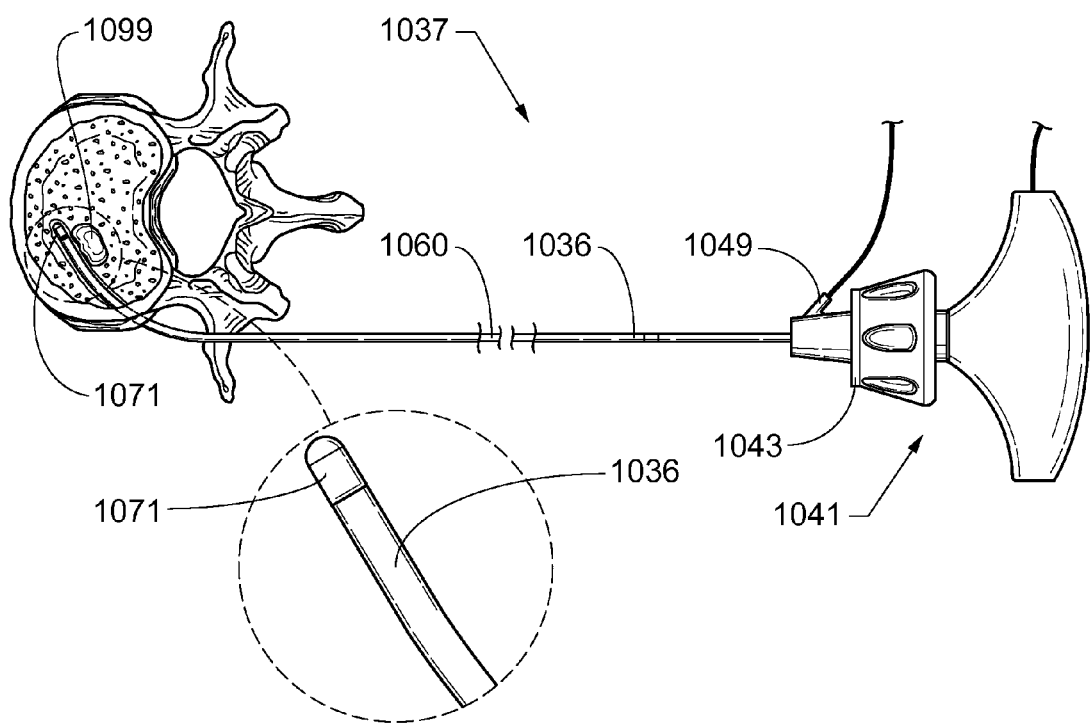
FIGS. 4A-4B show application of the pre-curved memory metal tissue ablation needle device to an intravertebral tissue mass.

The guide cannula 1022 and injection needle 1037 may be embodied and used in the manners disclosed in U.S. Pat. Nos. 7,713,273; 7,799,035; 7,922,690; 8,021,037; 8,128,633; 8,226,657; and 8,277,506; as well as U.S. Pat. Publ. Nos. 2011/00044220; 2012/0239047; and 2012/0277753, incorporated herein by reference. In one embodiment of a method of use, the guide cannula 1022 may be used to provide access into an intervertebral space. Then, as shown in FIG. 4A, the tissue ablation needle member 1037 can be directed through the guide cannula 1022 (not shown for sake of clarity) into the intravertebral space and into or immediately adjacent a target mass 1099 (e.g., tumor).

The tissue ablation needle member 1037 may be constructed in the manner of any of the embodiments disclosed herein (including by combining any features of any of said embodiments, or modifying them within the skill of those in the arts of electrosurgery and vertebroplasty). As shown, tissue ablation needle member 1037 includes an elongate needle cannula 1036 defining a needle lumen through which an inner probe 1060 extends. In FIG. 4A, the probe 1060 is not extended out from the needle cannula 1036, and the combined exterior of this needle assembly is used to cannulate a path to the target tissue 1099.

Then, the needle cannula 1036 is retracted to expose the electrodes of the inner probe 1060. In embodiments where the distal needle cannula tip is configured as an electrode, this same method may be applied to provide a variable-sized energy/ablation field that will be formed between a first electrode at or near the distal end of the inner probe with the distal needle cannula tip including the second electrode. Where the size of the field may controllably be varied relative to spacing between electrodes (e.g., making the field smaller by having them relatively close, or making the field larger/longer by having them further apart). Those of skill in the art will also appreciate that the method described here provides advantages with regard to lessening force upon (and increasing support of) the inner probe during advancement into target tissue, which may prevent distortion of and/or damage to the inner probe—particularly when the target tissue includes bone or other dense material.

Figure 4B:
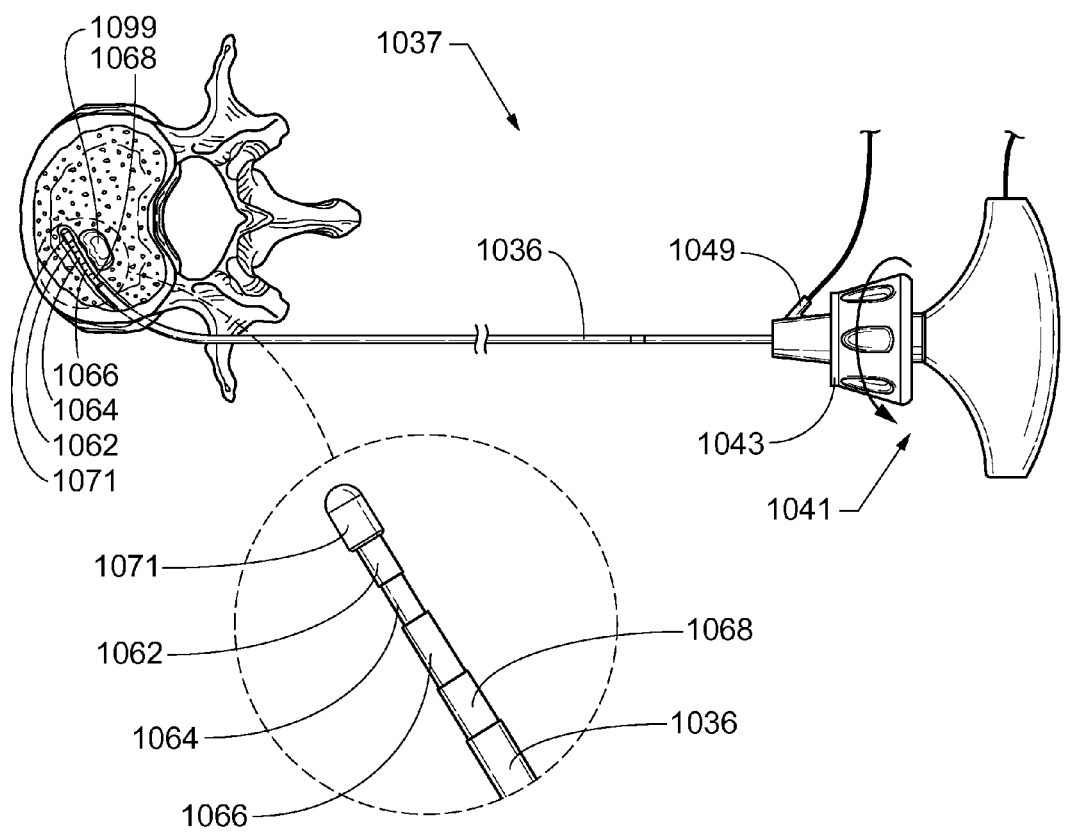

The inner probe 1060 includes an insulation-hard-coated distal tip 1071 (e.g., alumina-coated), a first electrode 1062, a first electroinsulative region 1064 (e.g., PEEK tube or sheath) separating the first electrode from a second electrode 1066, and a second electroinsulative coating layer 1068 that separates the second electrode 1066 from the needle cannula 1036. Wire(s) providing RF or other energy to the electrodes may be connected to the needle hub 1041 at a take-off 1049 and/or nearer the proximal end (depending upon a monopolar versus bipolar or other configuration, as will be appreciated by those of skill in the art). As shown, the take-off 1049 may be aligned with—and therefore used as externally visual indicia for—the direction of curvature of the distal needle end. The needle hub 1041 includes a rotary handle 1043 operably connected to the needle cannula 1036 in a manner that longitudinally retracts or extends the cannula 1036 relative to the probe 1060 when rotated. Those of skill in the mechanical arts will appreciate that a threaded interface or other any number of other mechanical interface means may be used to establish structure supporting this function. FIG. 4B shows the cannula 1036 having been retracted (e.g., by rotating the rotary knob handle 1043) to expose the electrodes 1062, 1066 for actuation to ablate the target mass 1099. FIGS. 4A and 4B each include a call-out view that shows the distal portion of the device in greater detail, without showing the surrounding tissue).

Upon completion of the ablation of the target mass 1099, the tissue ablation needle 1026 may be withdrawn from the guide cannula, and the Kyphoplasty balloon assembly 1091 introduced, and the distal-end balloon 1092 inflated to create a void. In some embodiments, the void may be filled through the coaxial cement injection cannula or the access cannula directly with a bone stabilization material. In other embodiments, the balloon 1092 may be withdrawn and the precurved injection needle introduced to complete injection of bone stabilization material (e.g., PMMA) into the void.

Those of skill in the art will appreciate that additional features may be included in different embodiments, and that those features will—as informed by the present disclosure—be practicable by those skilled in the art of designing and constructing electrosurgical medical devices. For example, a mechanical and/or electronic interlock may be included that will prevent activation of RF or other energy unless/until the internal probe is appropriately extended out of the needle cannula. On/off and magnitude control of the RF or other energy may be operable by hand and/or foot controls associated with the device and/or with an external generator. In most embodiments, impedance of electrical conductor components should be minimized (preferably less than about 2 ohms). Capacitance and Inductance of components should also be minimized to reduce indirect power loss in the system.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. For example, a system including the access/guide cannula and tissue ablation needle disclosed herein may be practiced in tissue other than bone, within the scope of the present embodiments and the present level of skill in the art. As another example, those of skill in the art will be able to use or readily adapt (with reference to the present disclosure and the current state of skill in the art) embodiments disclosed here to use bipolar or monopolar RF energy and/or microwave energy for tissue ablation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A tissue ablation needle system, comprising:
a rigid elongate guide cannula including an open proximal end, an open distal end, and a guide cannula lumen connecting therebetween;
an elongate needle cannula that circumferentially defines a needle lumen;
an elongate inner probe disposed through the needle lumen and configured to provide a distal needle tip of the needle cannula, where a probe distal end region includes a first electrode;
an electroinsulative layer disposed between the needle cannula and the first electrode; and a second electrode disposed proximal of the first electrode, wherein the needle cannula is formed of a continuous conductive material such that a distal end portion of the needle cannula includes the second electrode, where the needle cannula is retractable in the proximal direction relative to the inner probe to expose the probe distal end region at a location distal a needle cannula end, where the needle cannula is longer than the guide cannula such that the needle cannula distal region can be extended through and beyond a distal guide cannula end, released thereby from guide cannula lumen restraint, and where the distal needle tip comprises an outer diameter at least as large as an outer diameter of the needle cannula.

2. The system of claim 1, where the needle cannula includes a distal region pre-set, unjointed memory metal curve that can be substantially straightened to accommodate constrained passage through the guide cannula lumen and that includes a shape memory to assume the pre-set curve when unconstrained.

3. The system of claim 1, where the electroinsulative layer is disposed along a proximal length of the inner probe and forms an electroinsulative barrier between that proximal length and the needle cannula.

4. The system of claim 1, where the inner probe is slidable relative to the second electrode to a distance suitable to establish a tissue ablation radiofrequency field between the first electrode and the second electrode.

5. The system of claim 1, where a distal terminus of the inner probe includes the first electrode.

6. The system of claim 1, where the electroinsulative layer is disposed along and covering substantially an entire length of the inner probe except for the first electrode which is not covered by the layer.

7. The system of claim 1, where the first electrode is exposed around an entire external circumference of the inner probe.

8. The system of claim 1, where the first electrode is exposed around less than an entire external circumference of the inner probe, such that radiofrequency energy directed through the first electrode to the second electrode will not substantially traverse nor ablate tissue in a region immediately adjacent an unexposed portion of the first electrode.

9. The system of claim 1, where the first electrode is disposed immediately adjacent an electroinsulated distal end terminus of the inner probe.

10. The system of claim 1, where the guide cannula is about 11 gauge.

11. The system of claim 1, where a distal end tip of the inner probe is coated with an electroinsulative material, and the first electrode is immediately proximally adjacent thereto.

12. The system of claim 1, where the electroinsulative layer forms substantially an entire length of the inner probe except for at least one temperature sensor and a material forming a conductive path to at least one of the electrodes.

13. A kit for intravertebral tissue ablation, the kit including at least the system of claim 1, and further including at least one or more of a balloon assembly, a bone stabilization material delivery cannula, and a bone-penetrating guide cannula accessory.

14. The system of claim 1, where the inner probe is formed substantially of an electroinsulative material, and where the inner probe comprises a conductive path of communication connected to the first electrode.

15. The system of claim 1, where the inner probe further comprises a third electrode that is proximal of the first electrode.

16. A tissue ablation needle system, comprising:

a rigid elongate guide cannula including an open proximal end, an open distal end, and a guide cannula lumen connecting therebetween;

an elongate needle cannula that circumferentially defines a needle lumen;

an elongate inner probe disposed through the needle lumen and configured to provide a distal needle tip of the needle cannula, where a probe distal end region includes a first electrode;

an electroinsulative layer disposed between the needle cannula and the first electrode; and a second electrode disposed proximal of the first electrode, wherein the needle cannula is formed of a continuous conductive material such that a distal end portion of the needle cannula includes the second electrode, where at least one of the inner probe and the needle cannula is slidable relative to the other such that the inner probe extends through and beyond a distal needle cannula end, where the needle cannula is longer than the guide cannula such that the needle cannula distal end region can be extended through and beyond a distal guide cannula end, released thereby from guide cannula lumen restraint, and where the distal needle tip comprises an outer diameter at least as large as the outer diameter of the needle cannula to prevent the distal needle tip from being retracted into the needle cannula.

17. The system of claim 16, where the outer diameter of the distal needle tip forms a nearly continuous outer surface with the needle cannula.

* * * * *